US00PP35758P2

(12) United States Plant Patent
Hanna et al.

(10) Patent No.: US PP35,758 P2
(45) Date of Patent: Apr. 16, 2024

(54) CENTIPEDEGRASS NAMED 'TIFT TC458'

(50) Latin Name: *Eremochloa ophiuroides*
Varietal Denomination: Tift TC458

(71) Applicant: University of Georgia Research Foundation, Inc., Athens, GA (US)

(72) Inventors: Wayne W. Hanna, Chula, GA (US); Brian Schwartz, Tifton, GA (US); Sameer Khanal, Tifton, GA (US); J. Earl Elsner, Good Hope, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 18/125,903

(22) Filed: Mar. 24, 2023

(51) Int. Cl.
*A01H 5/00* (2018.01)
*A01H 6/46* (2018.01)

(52) U.S. Cl.
USPC ..... Plt./388

(58) Field of Classification Search
USPC ..... Plt./384, 388
See application file for complete search history.

*Primary Examiner* — Karen M Redden
(74) *Attorney, Agent, or Firm* — Thomas | Horstemeyer, LLP

(57) ABSTRACT

A new and distinct cultivar of Centipedegrass named 'Tift TC458' is provided. The new and distinct variety has excellent turf quality, increased seed head production, and increased nematode resistance as compared to similar commercial centipedegrass. The sexually and asexually reproduced diploid variety is reliably propagated both vegetatively and by seed.

4 Drawing Sheets

DESCRIPTION

Latin name: Centipedegrass 'Tift TC458' is of the genus and species *Eremochloa ophiuroides*.

Variety denomination: The new centipedegrass is denominated 'Tift TC458'.

BACKGROUND

The present invention relates to a new and distinct cultivar of centipedegrass botanically known as *Eremochloa ophiuroides* and has been given the varietal name 'Tift TC458'. The new *Eremochloa* 'Tift TC458' was collected and evaluated as a product of a breeding program conducted by the inventor in Tifton, Georgia. The objective of the centipedegrass breeding program is to create new plant cultivars with improved commercial qualities. This cultivar is commercially important for its excellent turfgrass quality, increased seed head production, increased nematode resistance, and other qualities, which are enumerated herein.

The pedigree and breeding history of 'Tift TC458' is described here and illustrated in the flow chart of FIG. 5. In August 1989 centipedegrass seeds (TC328 to TC337, all unpatented) were collected from old cemetery sites across southern Tennessee. These accessions were used to produce a random mating population (TC426, unpatented) in isolation at Tifton, Georgia in 1990.

In October of 1999, vegetative centipedegrass plants (TC338, unpatented) growing under shade near Changsha in the Hunan Province of China and seeds (TC340 and TC342, all unpatented) growing under heavy conifer shade near Quiyang in the Guizhou Province in China were collected. These accessions were increased under isolation at Tifton, Georgia in 2000. In May, 2000 the shade-tolerant accessions (TC338, TC340, and TC342) were seeded with 'TifBlair' (PVP No. 9600255, unpatented) breeder's seed under a fiberglass top rainout shelter with 60% shade, where the fiberglass was 1.8 meters above the plots. On 3 Sep. 2001, 50 of the most vigorous surviving clones were selected and established in an open sunlight plot. This plot became TC431, unpatented. The seed from random mating of TC431 became TC452 (all unpatented).

In July 2000, surviving plants were collected from the abandoned 'Oaklawn' centipedegrass foundation field near Perkins, Oklahoma (TC414, unpatented). Additional seeds were collected from surviving plants growing in weeds and on the range, from 1960's centipedegrass research at Ft. Cobb, Oklahoma (TC415, unpatented). A random mating population of these accessions (TC434, unpatented) was developed in 2001 in Tifton, Georgia.

In July 2000 centipedegrass from six cemetery sites across northern Tennessee was collected (TC408 to TC413, all unpatented). These accessions were used to develop a TC428 (unpatented) random mating population in Tifton, Georgia in 2001.

In April 2002 equal quantities of TC426, TC428, TC434, and 'TifBlair' were bulked, and seed planted in isolation at Tifton, Georgia. TC437 (unpatented) seed was harvested from this random mating 2002 plot in 2003. In June 2005 a replicated test of TC437 was planted in Blairsville, Georgia. In April 2005, 80% seed from TC437 and 20% seed from TC452 was bulked and planted in isolation, and the resultant product was put through four recurrent random mating cycles, planted in 2006, 2008, 2010, and 2012, from which seed was harvested in 2007, 2009, 2011 and 2013, respectively. The seed harvested in 2013 became 'Tift TC458'.

The new centipedegrass 'Tift TC458' was observed for genetic stability in Lakeland, Georgia from April 2015 through 2018. Observations indicated 'Tift TC458' was genetically stable within commercially acceptable limits.

The new centipedegrass 'Tift TC458' was observed for uniformity over five years, from 2015 to 2020, in Tifton, Georgia, Lakeland, Georgia, Marshallville, Georgia, Ft. Valley, Georgia, and Orangeburg, South Carolina. Observations indicated 'Tift TC458' was genetically uniform and stable within commercial acceptable limits.

From 2016 to 2018 replicated tests were planted in two locations in Georgia, a location in North Carolina, and a location in Illinois for comparison to the similar grass 'TifBlair'.

Asexual propagation of the new centipedegrass 'Tift TC458' via sprigs and sod was established in a controlled environment in Tifton, Georgia, and has continued since 2013. Observation of the 'Tift TC458' progeny has shown the unique features of this new centipedegrass are stable and reproduce true to type in successive generations.

SUMMARY

The cultivar 'Tift TC458' has not been observed under all possible environmental conditions. The phenotype may vary somewhat with variations in environment and cultural practices such as temperature water and fertility levels, soil types, and light intensity, however, without any variance in genotype. The following traits have been repeatedly observed and have been determined to be the unique combination of characteristics of 'Tift TC458'. In combination, these traits set 'Tift TC458' apart from all other existing varieties of centipedegrass known to the inventors:

1. Turf quality equal to or superior to the most improved centipede grasses on the market, as determined according to an industry standard visual turfgrass rating scale of 1 to 9 with 1=poor and 9=excellent, which is based on color, density, and texture of a species. A rating of 7 is considered acceptable turf quality,
2. Increased seed head production; and
3. Increased nematode resistance.

'Tift TC458' has been compared to the similar grass, 'TifBlair', as discussed and set forth in Tables below. The locations and time of year ratings were taken are provided in the Tables.

'Tift TC458' can be compared to commercial cultivar (and ancestor) 'TifBlair' in at least the following characteristics: 'Tift TC458' has an increased number of inflorescences than 'TifBlair'. The leaf width of 'Tift TC458' is wider than that of 'TifBlair'. The leaf length of 'Tift TC458' is longer than that of 'TifBlair'. 'Tift TC458' has an increased internode length as compared to 'TifBlair'. The number of total stolons of 'Tift TC458' is more than that of 'TifBlair'. The total stolon length of 'Tift TC458' is longer than that of 'TifBlair'. 'Tift TC458' has an increased canopy height over 'TifBlair'. 'Tift TC458' and 'TifBlair' have similar rates of stolon growth and spread. 'Tift TC458' and 'TifBlair' have similar sod densities and cold tolerance. 'Tift TC458' and 'TifBlair' are a similar color. 'Tift TC458' and 'TifBlair' have similar panicle lengths, though 'Tift TC458' has more florets per cm panicle length than 'TifBlair'. 'Tift TC458' and 'TifBlair' have similar stalk lengths.

TABLE 1

Turf quality of two centipedegrass cultivars seeded at Tifton, GA in 2014[1]. Turf Quality[2]

| | 2015[3] | | | | 2016[3] | | |
|---|---|---|---|---|---|---|---|
| Centipede Cultivar | 15 Apr | 6 June | 11 Aug | 28 Sept | 21 July | 12 Oct | 26 Oct |
| 'Tift TC458' | 8.5 | 8.4 | 8.6 | 9.0 | 8.8 | 9.0 | 8.8 |

TABLE 1-continued

Turf quality of two centipedegrass cultivars seeded at Tifton, GA in 2014[1]. Turf Quality[2]

| | | | | | | | | |
|---|---|---|---|---|---|---|---|---|
| 'TifBlair' | 8.4 | 7.8 | 8.2 | 9.0 | 8.2 | 9.0 | 8.8 | |
| LSD[4] | NS | 0.4 | 0.4 | NS | NS | NS | NS | |
| | 2017[3] | | | | 2018[3] | | | |
| Centipede Cultivar | 23 May | 7 July | 29 July | 17 Sept | 8 May | 7 June | 15 July | 8 Oct |
| 'Tift TC458' | 7.0 | 7.6 | 8.4 | 8.8 | 8.4 | 8.0 | 7.9 | 9.0 |
| 'TifBlair' | 6.7 | 7.4 | 8.2 | 8.8 | 8.2 | 7.6 | 7.0 | 8.8 |
| LSD[4] | NS | NS | NS | NS | NS | NS | 0.7 | NS |

[1]Tests planted 2 Jun. 2014 at Tifton, GA.
[2]Visual turfgrass rating scale of 1 to 9 with 1 = poor and 9 = excellent. A rating of 7 is considered acceptable turf quality.
[3]Year when ratings were made. Plots mowed weekly at 5 cm except in 2015, plots mowed weekly at 7.5 cm.
[4]Least significant difference at P ≤ 0.05. NS = non-significant.

TABLE 2

Turf quality of two centipedegrass cultivars planted at Blairsville, GA in 2005 and 2016. Turf Quality[1]

| | 2005 Test[2] | | | | | | | 2016 Test[3] |
|---|---|---|---|---|---|---|---|---|
| | 2006[4] | | | 2008[4] | | | | 2017[4] |
| Centipede Cultivar | 6 June | 6 July | 18 Oct | 6 June | 9 June | 6 Aug | 26 Sept | 7 June |
| 'TC458' | 7.6 | 8.6 | 9.0 | 8.0 | 8.7 | 8.7 | 9.0 | 8.0 |
| 'Tift TifBlair' | 7.0 | 8.3 | 9.0 | 7.7 | 8.7 | 8.7 | 9.0 | 7.0 |
| LSD[5] | NS | NS | NS | NS | NS | NS | NS | 0 |

[1]Visual turfgrass rating scale of 1 to 9 with 1 = poor and 9 = excellent. A rating of 7 is considered acceptable turf quality.
[2]Test planted 25 Jun. 2005 at Blairsville, GA.
[3]Test planted 2 Jun. 2016 at Blairsville, GA.
[4]Year when ratings were made.
[5]Least significant difference at P ≤ 0.05. NS = non-significant.

TABLE 3

Turf quality of two centipedegrass cultivars seeded at Tifton, GA in 2016. Turf Quality[1]

| | Test 2016A[2] | | | | | Test 2016B[3] |
|---|---|---|---|---|---|---|
| | 2017[4] | 2018[4] | | | | 2018[4] |
| Centipede Cultivar | 17 Sept | 11 Apr | 8 May | 7 June | 17 July | 8 Oct |
| 'Tift TC458' | 8.8 | 8.0 | 8.5 | 8.8 | 8.0 | 8.3 |
| 'TifBlair' | 8.8 | 7.0 | 9.0 | 8.3 | 7.2 | 8.0 |
| LSD[5] | NS | NS | NS | NS | NS | NS |

| | Test 2016B[3] 2018[4] | | | | |
|---|---|---|---|---|---|
| Centipede Cultivar | 11 Apr | 8 May | 7 June | 17 July | 8 Oct |
| 'Tift TC458' | 7.8 | 8.0 | 8.5 | 8.5 | 8.8 |

TABLE 3-continued

Turf quality of two centipedegrass cultivars seeded at Tifton, GA in 2016.

| | Turf Quality[1] | | | | |
|---|---|---|---|---|---|
| 'TifBlair' | 7.8 | 8.0 | 7.7 | 8.3 | 8.5 |
| LSD[5] | NS | NS | 0.7 | NS | NS |

[1]Visual turfgrass rating scale of 1 to 9 with 1 = poor and 9 = excellent. A rating of 7 is considered acceptable turf quality.
[2]Test planted 1 Jun. 2016 at Tifton, GA on methyl bromide treated soil.
[3]Test planted 7 Jul. 2016 at Tifton, GA on native soil.
[4]Year when ratings were made.
[5]Least significant difference at P ≤ 0.05. NS = non-significant.

TABLE 4

Turf characteristics of two centipedegrass cultivars sodded in St. Peter, Illinois and Fletcher, North Carolina.

| | Illinois[1] | | | | N. Carolina[2] | | |
|---|---|---|---|---|---|---|---|
| | % Cover[3] | | | Turf Quality[4] | % Cover[3] | Turf Quality[4] | % Cover[3] |
| | 2017[5] | | 2018[5] | | 2017[5] | | 2018[5] |
| Centipede cultivar | 23 May | 1 Sept | 21 Nov | 17 Oct | 1 June | 22 Aug | 1 Oct |
| 'Tift TC458' | 37 | 68 | 81 | 2.9 | 96 | 9.0 | 78 |
| 'TifBlair' | 52 | 76 | 83 | 2.7 | 65 | 8.3 | 40 |
| LSD[6] | NS | NS | NS | 0.1 | NS | NS | NS |

[1]Test planted 15 Jun. 2016 at St. Peter, IL on a home lawn.
[2]Test planted 3 Jun. 2016 at a sod farm in Fletcher, NC.
[3]Percent ground surface covered by leaves and stolons.
[4]Visual turfgrass rating scale of 1 to 9 with 1 = poor and 9 = excellent. A rating of 7 is considered acceptable turf quality. Data transformed by square root. Actual values were 8.3 for TC458 and 7.7 for 'TifBlair'.
[5]Year when ratings were made.
[6]Least significant difference at P ≤ 0.05. NS = non-significant.

TABLE 5

Weekly canopy heights of two centipedegrass cultivars at Tifton, GA in 2016 on 2014 test[1].

| Centipede | Canopy height (mm)[2] | | | | |
|---|---|---|---|---|---|
| cultivar | 22 July | 1 Aug | 8 Aug | 15 Aug | 22 Aug |
| 'Tift TC458' | 42 | 62 | 73 | 81 | 88 |
| 'TifBlair' | 38 | 51 | 62 | 68 | 73 |
| LSD[3] | NS | 8 | 7 | 8 | NS |

[1]Test planted 2 Jun. 2014 at Tifton, GA.
[2]Height from ground level to top of leaf canopy. Mowed at 37 mm on 20 Jul. 2016 and mowing discontinued until after 22 Aug. 2016.
[3]Least significant different at P ≤ 0.05.
NS = non-significant.

TABLE 6

Number of stubby root nematodes (*Paratrichodorus* sp.) in two centipedegrass cultivars planted at two locations.

| | Number of nematodes[1] | | | | | | | |
|---|---|---|---|---|---|---|---|---|
| Centipede | Tifton 2014[2] | | | Tifton 2016A[3] | | Tifton 2016B[4] | | Blairsville 2016[5] |
| cultivar | 2016[6] | 2017[6] | 2018[6] | 2017[6] | 2018[6] | 2017[6] | 2018[6] | 2017[6] |
| 'Tift TC458' | 3.2 | 7.2 | 1.0 | 2.7 | 9.2 | 0 | 1.5 | 0 |

TABLE 6-continued

Number of stubby root nematodes (*Paratrichodorus* sp.) in two centipedegrass cultivars planted at two locations.

| | Number of nematodes[1] | | | | | | | |
|---|---|---|---|---|---|---|---|---|
| Centipede | Tifton 2014[2] | | | Tifton 2016A[3] | | Tifton 2016B[4] | | Blairsville 2016[5] |
| cultivar | 2016[6] | 2017[6] | 2018[6] | 2017[6] | 2018[6] | 2017[6] | 2018[6] | 2017[6] |
| 'TifBlair' | 20.5 | 8.6 | 0.6 | 13.7 | 24.3 | 0.3 | 7.5 | 0.5 |
| LSD[7] | NS | NS | NS | NS | 12.3 | NS | 5.9 | NS |

[1]Number of nematodes per 100 $cm^3$ soil.
[2]Test planted at Tifton, GA on 2 Jun. 2014.
[3]Test planted at Tifton, GA on 1 Jun. 2016.
[4]Test planted at Tifton, GA on 7 Jul. 2016.
[5]Test planted at Blairsville, GA on 2 Jun. 2016.
[6]Year samples were taken. Samples taken 27 October in 2016, 14 August in 2017, and 12 September in 2018 at Tifton, GA and 16 Aug. 2017 at Blairsville, GA.
[7]Least significant difference P ≤ 0.05. NS = non-significant.

TABLE 7

Number of three nematodes species in two centipedegrass cultivars planted at three locations.

| | Number of nematodes[1] | | | | |
|---|---|---|---|---|---|
| | Tifton 2014[2] | | | Tifton 2016B[3] | |
| Centipede | Ring[6] | Lesion[8] | Ring[6] | Ring[6] | |
| cultivar | 2017[7] | 2017[7] | 2018[7] | 2017[7] | 2018[7] |
| 'Tift TC458' | 0.4 | 0.0 | 8.8 | 121.0 | 1.5 |
| 'TifBlair' | 1.2 | 0.2 | 2.2 | 67.1 | 62.3 |
| LSD[12] | NS | NS | NS | NS | NS |

| | Number of nematodes[1] | | |
|---|---|---|---|
| | Blairsville[4] | North Carolina[5] | |
| Centipede cultivar | Ring[6] 2017[9] | Ring[6] 2017[10] | Spiral[11] 2017[10] |
| 'Tift TC458' | 6.5 | 35 | 0 |
| 'TifBlair' | 12.7 | 219 | 8.6 |
| LSD[12] | NS | NS | NS |

[1]Number of nematodes per 100 $cm^3$ soil.
[2]Test planted at Tifton, GA on 2 Jun. 2014.
[3]Test planted at Tifton, GA on 7 Jul. 2016.
[4]Test planted at Blairsville, GA on 2 Jun. 2016.
[5]Test planted at Fletcher, NC on 3 Jun. 2016.
[6]*Mesocriconema* sp.
[7]Year samples were taken. Samples taken 14 August in 2017 and 12 September in 2018.
[8]*Pratylenchus* sp.
[9]Year samples were taken. Samples taken 16 Aug. 2017.
[10]Year samples were taken. Samples taken 17 Aug. 2017.
[11]*Helicotylenchus* sp.
[12]Least significant difference P < 0.05. NS = non-significant.

TABLE 8

Turf characteristics of two centipedegrass cultivars grown under 95 to 75% shade[1].

| Centipede cultivar | Turfgrass quality[2] 2017[3] 7 July | 28 July | 17 Sept | 2018[3] 7 June | 17 July | 8 Oct | 2017/2018[4] 95% | 90% | 75% |
|---|---|---|---|---|---|---|---|---|---|
| 'Tift TC458' | 4.6 | 3.0 | 3.6 | 5.3 | 5.6 | 5.7 | 3.2 | 5.4 | 7.4 |
| 'TifBlair' | 4.3 | 2.3 | 2.3 | 5.0 | 5.0 | 4.3 | 3.5 | 3.6 | 7.6 |
| LSD[5] | NS | NS | NS | NS | NS | NS | NS | 0.5 | NS |

[1]Measured photosynthetic active radiation at ground level relative to conditions under full sunlight under a rainout shelter with fiberglass roof 1.8 m above the plots.

[2]Visual turfgrass quality rating on scale of 1 to 9 with 1 = poor and 9 = excellent. A rating of 7 is considered acceptable turf quality.

[3]Year ratings were recorded for entries in a randomized complete block with three replications and included putative shade tolerant *Zoysia* sp. cultivars. Shade for replications 1, 2, and 3 were 95, 90, and 75%, respectively due to fiberglass discolorations.

[4]Ratings at each date in 2017 and 2018 were used as replications for each cultivar for each 95, 90, and 75% shade.

[5]Least significant difference P < 0.05. NS = non-significant.

TABLE 9

Turf characteristics of two centipedegrass cultivars grown under 73% shade[1].

| Centipede cultivar | 2017[2] Turf Quality[3] 3 Mar | 7 July | 28 July | 17 Sept | Area Covered[4] ($cm^2$) 7 Apr |
|---|---|---|---|---|---|
| 'Tift TC458' | 7.3 | 7.6 | 8.0 | 8.3 | 1293 |
| 'TifBlair' | 4.0 | 7.0 | 7.3 | 7.6 | 738 |
| LSD[6] | NS | NS | NS | NS | 181 |

| Centipede cultivar | 2017[2] Turf Quality[3] 11 Apr | 7 June | 17 July | 8 Oct | 2018[2] Height[5] (cm) 7 June | 17 July |
|---|---|---|---|---|---|---|
| 'Tift TC458' | 7.6 | 8.0 | 8.6 | 5.6 | 11.6 | 12.3 |
| 'TifBlair' | 7.6 | 8.0 | 7.6 | 4.6 | 11.3 | 11.0 |
| LSD[6] | NS | NS | NS | NS | NS | NS |

[1]Measured photosynthetic active radiation at ground level relative to conditions under full sunlight. Under a gusset hut frame covered with 73% shade cloth.

[2]Year ratings were taken.

[3]Visual turfgrass quality rating on scale of 1 to 9 where 1 = poor and 9 = excellent. A rating of 7 is considered acceptable.

[4]Average width × average length of grass area established in plot.

[5]Height from ground level to top of leaf canopy.

[6]Least significant difference P ≤ 0.05. NS = non-significant.

TABLE 10

Seed set and influorescence numbers for two centipedegrass cultivars.

| Centipede cultivar | 2017[1] Number of influorescences[2] 2014 Test[3] | 2016 A Test[4] | 2016 B Test[5] | 2018[1] % Seed Set 2014 Test | 2016 A Test[4] | 2016 B Test[5] |
|---|---|---|---|---|---|---|
| 'Tift TC458' | 233 | 314 | 410 | 347 | 93 | 89 | 89 |
| 'TifBlair' | 172 | 216 | 188 | 261 | 87 | 87 | 87 |
| LSD[6] | 36 | 37 | 57 | 47 | 4 | NS | NS |

[1]Year data was recorded.

[2]Number of influorescences per 900 $cm^2$. Influorescences counted 18 Sep. 2017 and 22 Aug. 2018.

[3]Test planted 2 Jun. 2014

[4]Test planted 2 Jun. 2016.

[5]Test planted 7 Jul. 2016.

[6]Least significant difference P < 0.05. NS = non-significant.

TABLE 11

Leaf and plant characteristics of individual plants of two centipedegrass cultivars.

| Centipede cultivar | Plant Diameter[1] (cm)[2] | Leaf Width[4] (mm)[3] | Leaf Length[4] (cm)[3] | Internode Length[4] (cm)[4] | Total Stolons per Plant[5] (#) | Total Stolon Length Per Plant[5] (cm) |
|---|---|---|---|---|---|---|
| 'Tift TC458' | 115 | 4.4 | 7.5 | 3.0 | 4.5 | 103 |
| 'TifBlair' | 108 | 4.1 | 6.6 | 2.9 | 3.2 | 81 |
| LSD[6] | NS | 0.2 | 0.4 | 0.1 | 0.5 | 15 |

[1]110 random plants from each cultivar planted in 72-hole flats in the greenhouse on 23 Mar. 2015 and transplanted to the field on 1.2 m centers on 27 Apr. 2015.

[2]Average plant diameter on 23 Jun. 2015.

[3]Average width and length of 2 leaves from the last elongated internode from two stolons on each plant on 22 Jul. 2015.

[4]Average length of the last elongated internodes from two stolons from each plant on 22 Jul. 2015.

[5]Average of 100 plants of each cultivar planted in 10 cm pots growing in the greenhouse spaced on 20 cm centers. Experiment was planted 22 Sep. 2016 in steam-sterilized soil and measurements were taken on 9 Dec. 2016. Characteristics measured were total stolons per plant and total stolon length per plant.

[6]Least significant difference P ≤ 0.05. NS = non-significant.

TABLE 12

Summarized various color characteristics, size, ligule type, auricles, collar type, and surface texture characteristics, and venation of 'Tift TC458'.

| Characteristic | Description (mean ± standard Error) |
|---|---|
| Fertile floret lemma length (mm) | 2.74 ± 0.01 (n = 16) |
| Fertile floret lemma width (mm) | 1.04 ± 0.12 (n = 16) |
| Fertile floret palea length (mm) | 2.08 ± 0.42 (n = 16) |
| Fertile floret palea width (mm) | 0.86 ± 0.26 (n = 16) |
| Sterile floret length (mm) | 3.15 ± 0.39 (n = 16) |
| Sterile floret width (mm) | 0.36 ± 0.11 (n = 16) |
| Glume length (mm) | 3.72 ± 0.48 (n = 16) |
| Glume width (mm) | 1.50 ± 0.11 (n = 16) |
| Awn length (mm) | Absent |
| Fertile floret palea color | Opaque, membraneous |
| Fertile floret lemma color | Opaque, membraneous |
| Glume color | Yellow-Green Group 147B mottled with Greyed-Purple Group 184A (mainly on margins) |
| Sterile floret color | Yellow-Green Group 147C |
| Stolon color in canopy | Yellow-Green Group 146B |
| Ligule color | Opaque, Membraneous |
| Sheath color | Yellow-Green Group 146D (base) to 146C (top) |
| Collar color | Yellow-Green Group 145B |
| Average length of sheath (cm) | 2.75+ 0.21 (n=16) |
| Ligule type | Membraneous with hairs less than 1 mm long |

TABLE 12-continued

Summarized various color characteristics, size, ligule type, auricles, collar type, and surface texture characteristics, and venation of 'Tift TC458'.

| Characteristic | Description (mean ± standard Error) |
|---|---|
| Auricle type | Absent |
| Collar type | Continuous |
| Adaxial leaf surface texture | Smooth |
| Abaxial leaf surface texture | Smooth |
| Adaxial leaf surface color | Yellow-Green Group 146B |
| Abaxial leaf surface color | Yellow-Green Group 146B |
| Leaf venation color | Folded |

The foregoing and other objects, features, and advantages of the invention will become more apparent from the following detailed description, which proceeds with reference to the accompanying figures.

BRIEF DESCRIPTION OF THE DRAWINGS

The accompanying colored photographic illustrations show the overall appearance and distinct characteristics of the new cultivar of the new *Eremochloa ophiuroides*. centipedegrass named 'Tift TC458' showing the colors as true as possible. Colors in the photographs may differ slightly from the color values cited in the detailed botanical description, which accurately describes the colors of the new 'Tift TC458'.

DETAILED BOTANICAL DESCRIPTION

Figure 1:
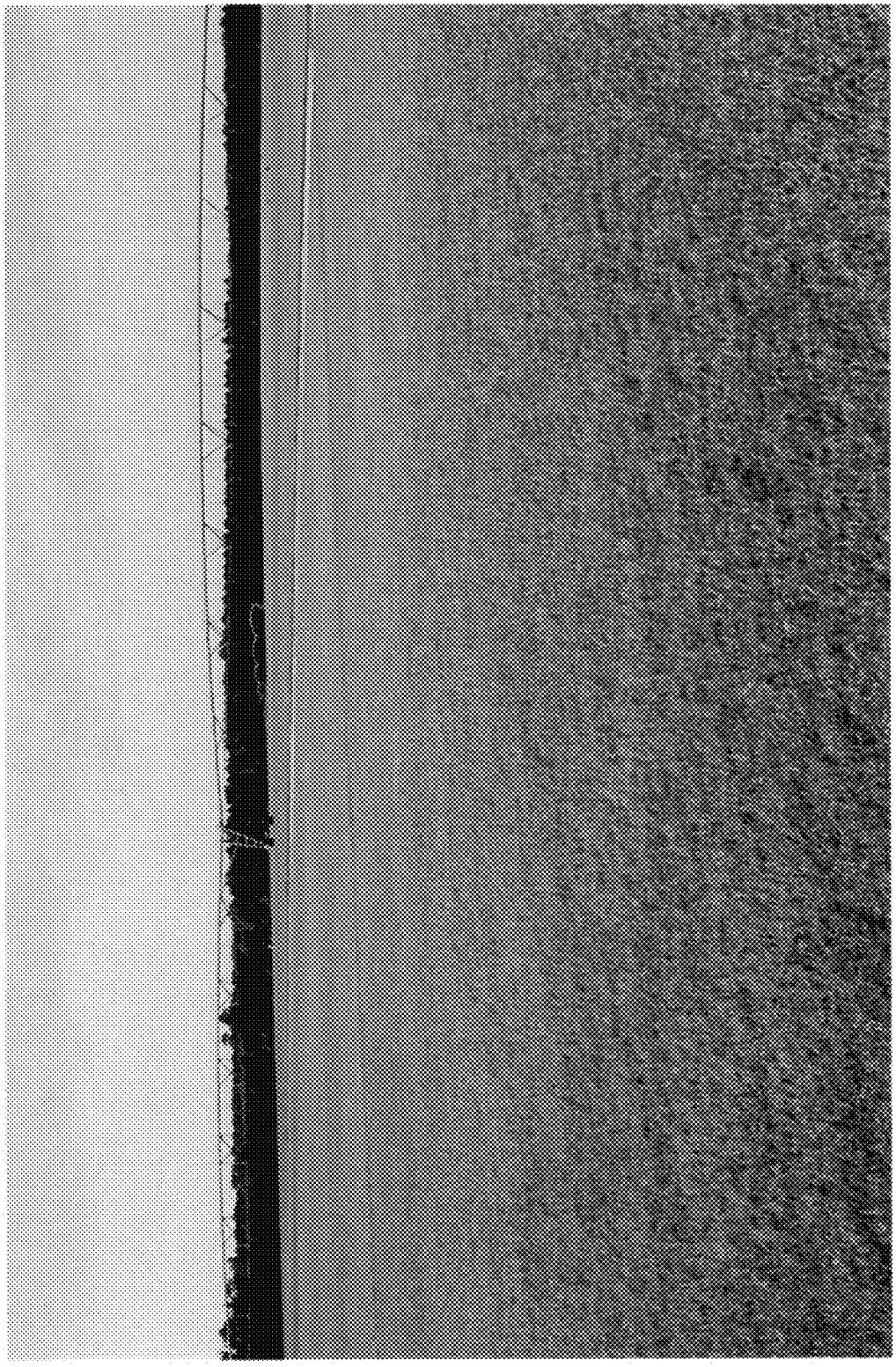
FIG. 1 is a photograph of 'Tift TC458' planted in a field (foreground) showing superior turf quality under low maintenance. The photograph was taken of the plots in a field in Lakeland, GA on Jul. 12, 2017. The trial was planted in April 2016.
Figure 2:
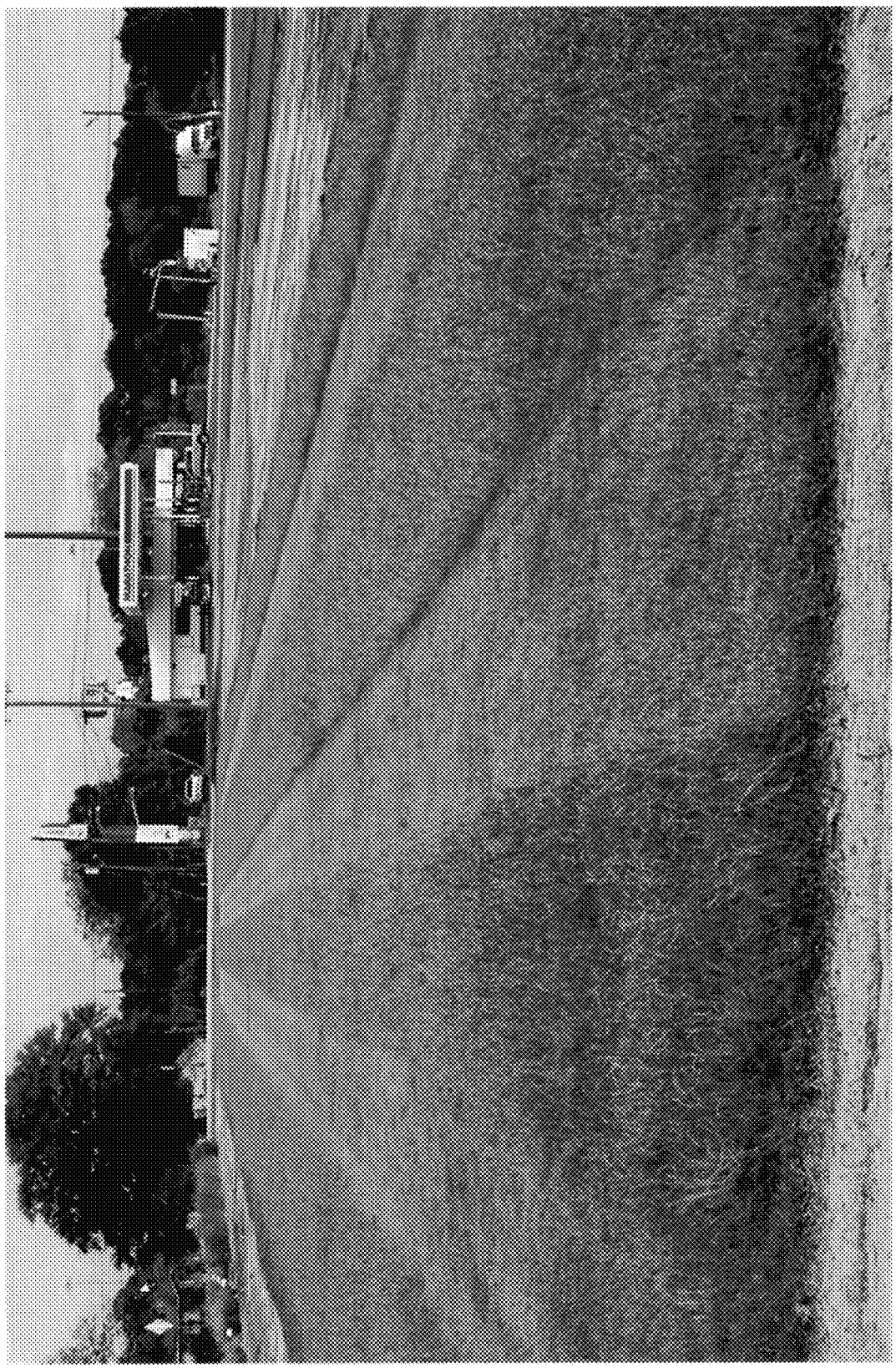
FIG. 2 is a photograph of 'Tift TC458' centipedegrass showing dense seed heads. The photograph was taken of the plots in a field in Tifton, GA on Nov. 2, 2019. The trial was planted in April 2014.
Figure 3:
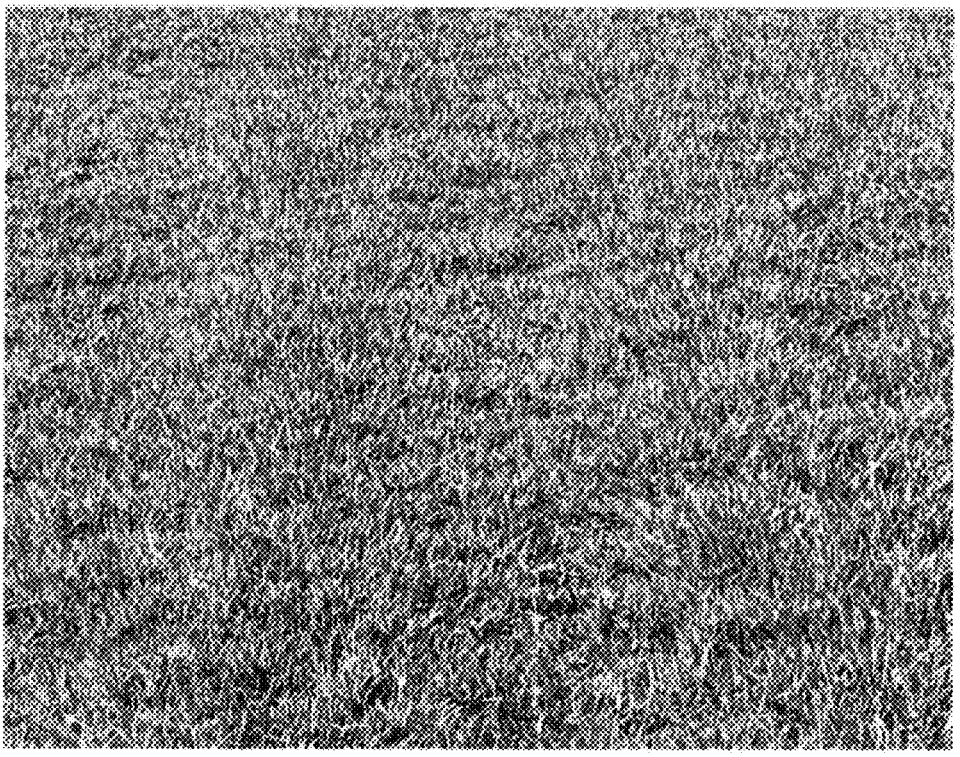
FIG. 3 is a close-up photograph of 'Tift TC458' planted in a field showing superior turf quality. The photograph was taken of the plot in a field in Foley, AL on Nov. 14, 2022. The trial was planted in July 2022.
Figure 4:
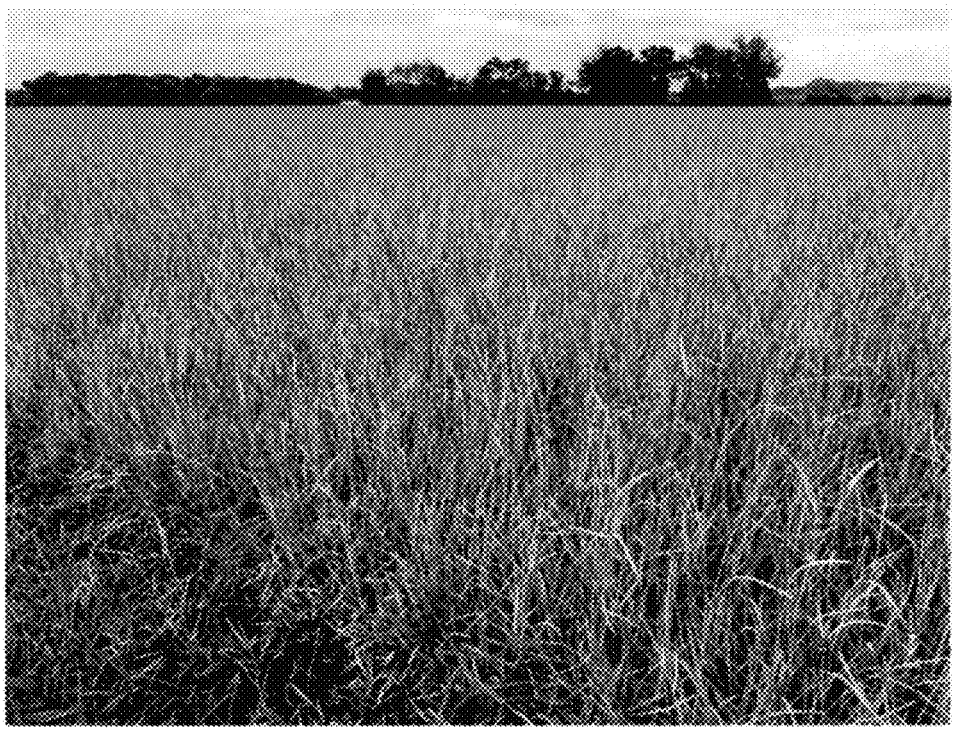
FIG. 4 is a close-up photograph of 'Tift TC458' showing dense seed heads. The photograph was taken of the plots in a field in Ft. Valley, GA on Aug. 5, 2019. The trial was planted in March 2018.
Figure 5:
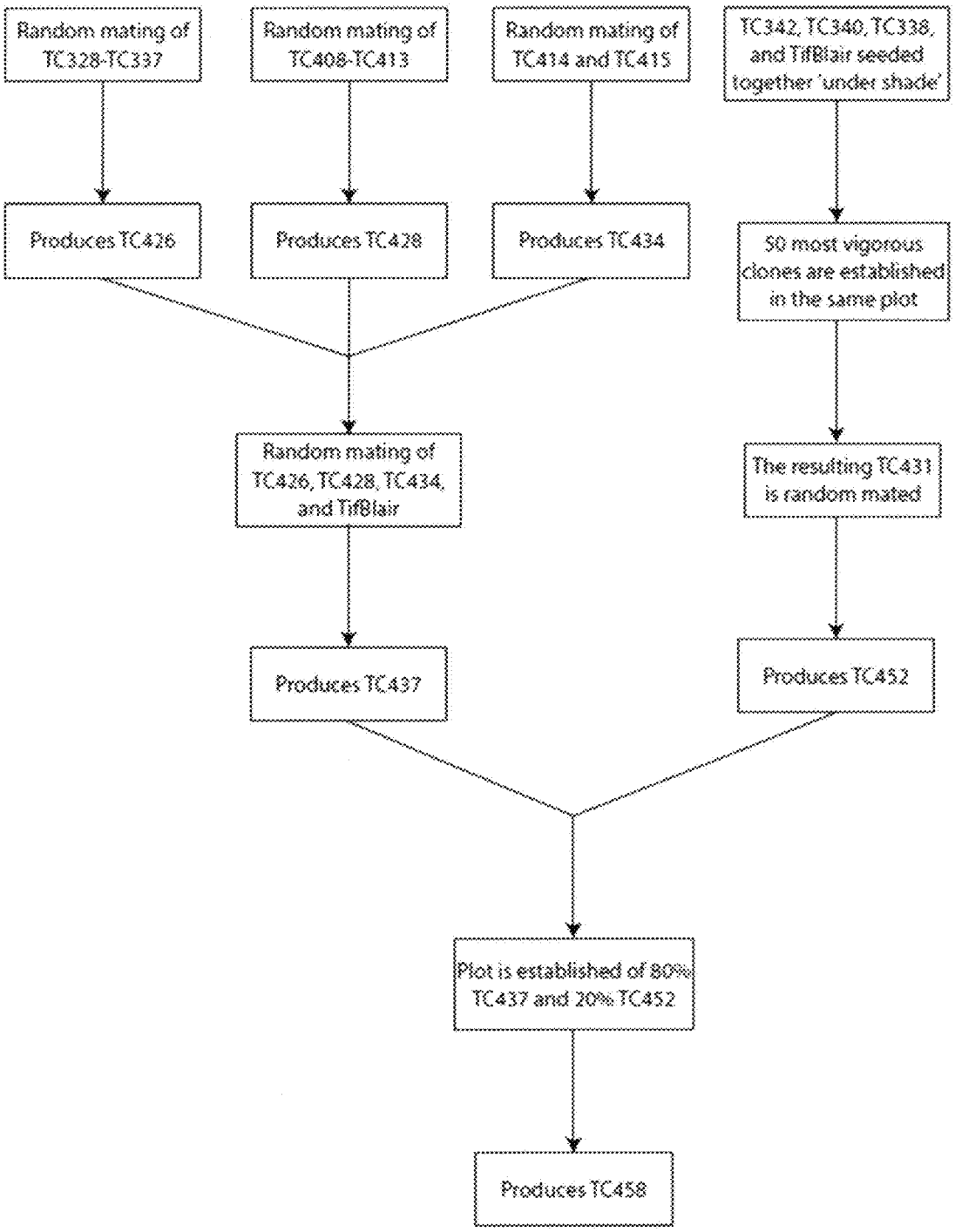
FIG. 5 is a flow chart illustrating the breeding history of 'Tift TC458'.

The following observations, measurements, and values describe 'Tift TC458' plants grown in Tifton, Georgia and other locations in the United States. The following traits have been consistently observed and, to the best knowledge of the inventors, their combination forms the unique characteristics of the new variety 'Tift TC458'. During the growing of the plants, typical day temperatures in Tifton, GA from April 1 to October 30 ranged from about 70° F. to 91° F., and typical night temperatures ranged from about 50° F. to 73° F.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

'Tift TC458' has adaxial and abaxial leaf color Yellow-Green Group 146B and internode color Greyed-Purple Group 185B (when exposed to direct sunlight) of R.H.S. Infrequent green-stemmed plants have leaf and internode colors of Yellow-Green Group 146A and Yellow Group 145C, respectively. The similarity of leaf colors for the two plant types makes them almost indistinguishable at the vegetative stage. 'Tift TC458' has anther color Red-Purple Group 59A and stigma color Red-Purple Group 62C. The green stemmed plants have anther and stigma colors of Yellow Group 4D and White Group 155D, respectively. The green-stemmed plants can most easily be identified at anthesis due to anther and stigma color.

'Tift TC458' is a diploid. It can be propagated by both seeds or vegetatively, by sprigs or sod.

'Tift TC458' Turf Quality is compared to 'TifBlair' (Tables 1-4). Ratings were taken over multiple years at multiple locations including Tifton, Georgia (Table 1 and Table 3), Blairsville, Georgia (Table 2), St. Peter, Illinois (Table 4), and Fletcher, North Carolina (Table 4). 'Tift TC458' has performed well for five years in northern Georgia where the average low temperatures range from −13 C to −17 C. Although centipedegrass is known as a drought tolerance species, 'Tift TC 458' was not tested for drought tolerance. 'Tift TC458' combines the very best centipedegrass germplasm from diverse environmental areas, as described in the breeding history, to give this cultivar broad adaptation.

'Tift TC458' had greater canopy heights than 'TifBlair' when left un-mowed for approximately 30 days in Tifton, Georgia (Table 5).

'Tift TC458' consistently had fewer Stubby Root, Spiral, and Lesion (*Pratylenchus*) nematodes than 'TifBlair' (Tables 6-7). The number of stubby root nematodes was counted in Tifton, Georgia and Blairsville, Georgia (Table 6). The number of three nematode species (*Mesocriconema, Pratylenchus,* and *Helicotylenchus*) was determined in Tifton, Georgia, Blairsville, Georgia, and Fletcher, North Carolina (Table 7).

'Tift TC458' has similar or better turfgrass quality in comparison to 'TifBlair' when grown under 95% to 75% shade in a rainout shelter with a fiberglass roof 1.8 m above the plots under (Table 8). When both centipedegrass cultivars were grown under a gusset hut frame covered with 73% shade cloth, 'Tift TC458' again had similar or better turf quality (Table 9). 'Tift TC458' additionally covered a larger area in comparison to 'TifBlair' and had a higher canopy height (Table 9).

'Tift TC458' produced 36% to 57% more seed heads than 'TifBlair' with equal seed set (Table 10). This favors higher seed production to lower seed production costs.

The morphological traits of 'Tift TC458' were evaluated in Table 11. 'Tift TC458' has a wider leaf width than 'TifBlair' (Table 11). 'Tift TC458' has a longer leaf length than 'TifBlair' (Table 11). 'Tift TC458' has an increased number of stolons per plant than 'TifBlair', with an increased stolon length (Table 11).

In addition to the data provided in the Summary of the Invention, the turf density and leaf texture of centipedegrass 'Tift TC458' are considered intermediate compared to other warm-season turfgrasses. They are similar to seeded common bermudagrass or 'Meyer' (unpatented) zoysiagrass and coarser than 'Tifway' (unpatented) bermudagrass and denser than St. Augustine grass cultivars.

No diseases have been observed on 'Tift TC458' in any year or at any testing site. Centipedegrass does not have any obvious diseases. Mosaic viruses can probably be found on all centipedegrass by assay methods, but the viruses cannot be visually rated and do not have apparent adverse effects on plant performance.

We claim:

1. A new and distinct variety of the centipedegrass plant named 'Tift TC458', substantially as illustrated and described herein.

* * * * *